United States Patent
Drössler et al.

(10) Patent No.: US 7,377,000 B2
(45) Date of Patent: **\*May 27, 2008**

(54) TOOTHBRUSH

(75) Inventors: Michael Drössler, Gehrden (DE);
Thomas Fritsch, Eppstein (DE);
Michael Harms, Oberursel (DE);
Armin Schwarz-Hartmann,
Wendelsheim (DE)

(73) Assignee: Braun GmbH, Kronberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/613,640

(22) Filed: Dec. 20, 2006

(65) Prior Publication Data

US 2007/0084002 A1    Apr. 19, 2007

Related U.S. Application Data

(60) Division of application No. 10/771,529, filed on Feb. 4, 2004, now Pat. No. 7,162,764, which is a continuation of application No. PCT/EP02/09417, filed on Aug. 23, 2002.

(30) Foreign Application Priority Data

Sep. 14, 2001 (DE) ................. 101 45 320
Feb. 16, 2002 (DE) ................. 102 06 493

(51) Int. Cl.
*A61C 17/34* (2006.01)
*A46B 13/02* (2006.01)

(52) U.S. Cl. ........................ 15/22.1; 15/28

(58) Field of Classification Search ............. 15/22.1, 15/28
See application file for complete search history.

(56) References Cited

U.S. PATENT DOCUMENTS

| 3,945,076 | A | 3/1976 | Sung |
| 4,791,945 | A | 12/1988 | Moriyama |
| 5,524,312 | A | 6/1996 | Tan et al. |
| 5,862,558 | A | 1/1999 | Hilfinger et al. |
| 6,349,442 | B1 | 2/2002 | Cohen et al. |
| 2003/0154567 | A1 | 8/2003 | Gehrden |

FOREIGN PATENT DOCUMENTS

| DE | 296 20 690 | 5/1998 |
| DE | 198 02 904 | 7/1999 |
| DE | 201 08 679 | 9/2001 |
| DE | 201 12 320 | 11/2001 |
| FR | 2228352 | 11/1974 |
| WO | WO 99/63905 | 12/1999 |

*Primary Examiner*—Randall Chin
(74) *Attorney, Agent, or Firm*—Fish & Richardson P.C.

(57) ABSTRACT

An electric toothbrush having a handpiece, a bristle holder which is arranged on a head portion of the handpiece and is rotatable about an axis of rotation of the bristle holder, and a drive mechanism for the bristle holder. The drive mechanism includes a motor which is arranged on the handpiece, and a transmission member which transfers a driving motion from the motor to the bristle holder. The transmission member is arranged to rock in multiple axes and is arranged to be driven by the motor such that is approximately traverses a double conical path.

16 Claims, 6 Drawing Sheets

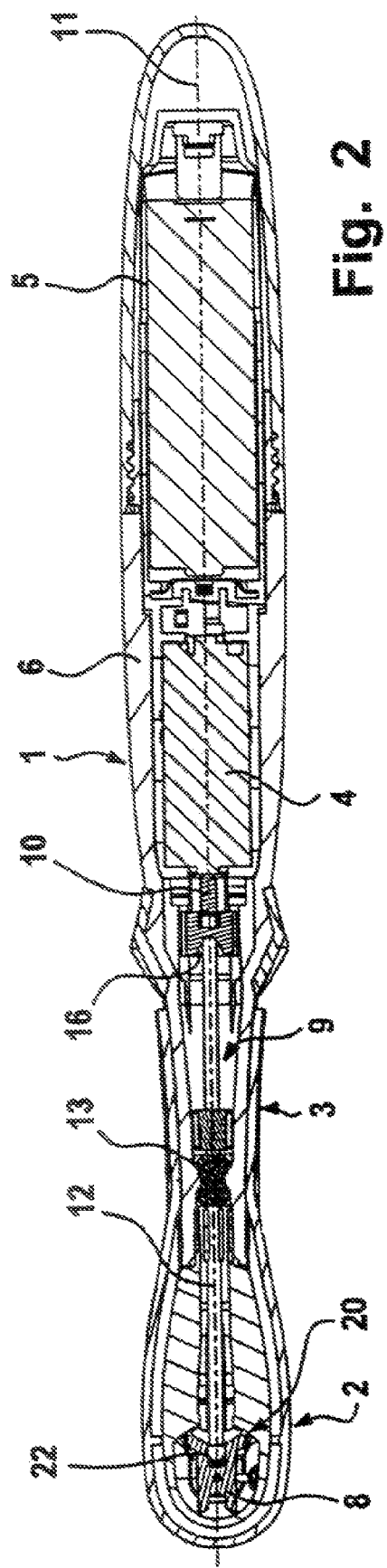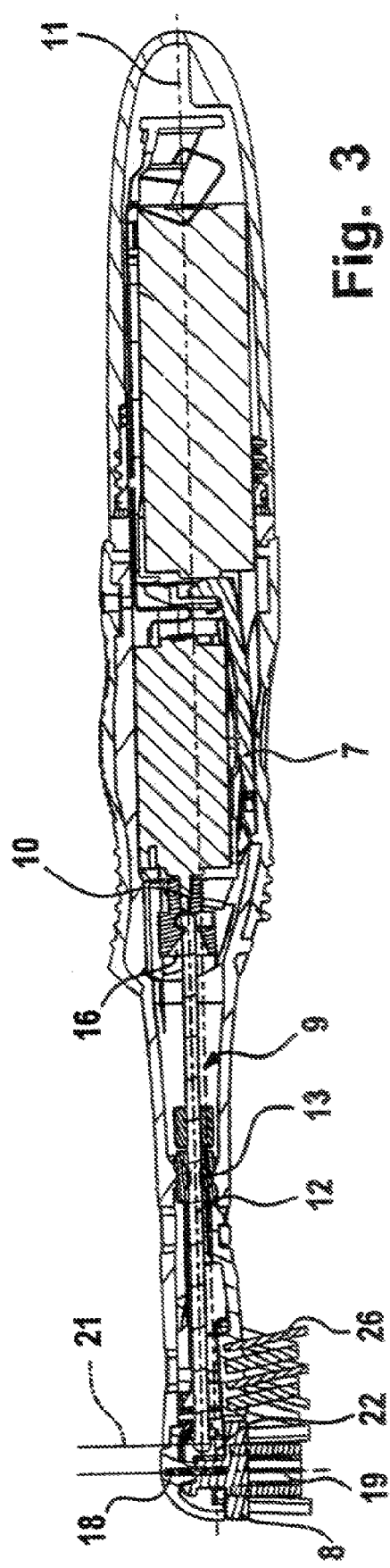

TOOTHBRUSH

CROSS REFERENCE TO RELATED APPLICATIONS

This is a divisional of U.S. application Ser. No. 10/771,529, filed Feb. 4, 2004, now U.S. Pat. No. 7,162,764, which is a continuation of PCT Application No. PCT/EP02/09417, filed Aug. 23, 2002, claiming priority from German application number 101 45 320.5, filed Sep. 14, 2001 and German application number 102 06 493.8, filed Feb. 16, 2002. The entire contents of the above-referenced U.S. and PCT applications are incorporated by reference.

TECHNICAL FIELD

The present invention relates to an electric toothbrush.

BACKGROUND

A toothbrush of the kind described is known from WO 01/19281 A2, according to which an approximately round bristle cluster is drivable in a rotary oscillating manner. A bristle holder that is rotatably arranged in the brush head is coupled to a transmission member, which is driven back and forth lengthwise by a crank that is attached to a gearwheel. However, a crank drive of such kind has a relatively large space requirement. Moreover, because of the components it requires, it is complex and expensive. Thus, it is only practical for use in highly priced toothbrushes.

An electric toothbrush in which the rotary drive motion of the motor is transmitted to the bristle holder by a transmission member is known from U.S. Pat. No. 4,149,291. This transmission member is eccentrically coupled to the drive shaft at one end, and is supported by a ring bearing at its other end, where it exits the handpiece, so that it describes a conical driveing motion. In order to impart a special, approximately elliptical motion to the detachable brush element that is seated on the transmission member, the transmission member includes a spring that flexes along one axis. As a result the conical driving motion of the transmission member is only transferred to a limited degree in this one axis. However, because of the sophisticated design of the transmission member, this drive is complicated and expensive. Additionally, because of its spring-driven configuration, it is prone to fatigue. Moreover, the elliptical drive motion of the toothbrush head is in many respects disadvantageous.

German Patent No. DE 20112320 U1 described another electric toothbrush, in which the brush holder, with the bristle cluster affixed thereto, is arranged rigidly at one end of a drive rocker, which is disposed inside a hollow brush handle. The drive rocker is arranged to rock in multiple axes and is excited to oscillate in two axes by piezoelectric elements that are arranged at the other end of the drive rocker, between the rocker and the internal wall of the brush handle. However, the bristle holder, which is securely affixed to the rocker end, performs only relatively small, tethered movements. Particularly, rotating movements that turn the bristle cluster in on itself cannot be performed to a degree that would yield an optimum result in terms of cleaning the teeth.

SUMMARY

In one aspect, a transmission member is provided that is disposed so as to be rockable in multiple axes and is drivable by a motor such that it performs a movement that approximates a double cone. The connection between the driver rocker and the bristle holder is conformed in a jointed manner about an articulated axis that is parallel to the bristle holder's axis of rotation. The ends of the transmission rocker experience circular or elliptical movements. The bristle holder does not perform a directly corresponding movement, because it is not rigidly a fixed to the end of the transmission rocker. The bristle holder is rotatable supported about a fixed axis of rotation and is also separated from the connection with the rocker at the handpiece or the head section of the housing of the toothbrush. This articulated connection with the transmission rocker allows rotary oscillation about the bristle holder's axis of rotation.

The transmission rocker is supported in a section between its free ends in such manner that the two portions of the drive rocker located to the left and right of the bearing each traverse the envelope of a cone, particularly a rounded cone, the vertices of which are situated in the area of the bearing.

In one embodiment, at least a part of the motion of the driver rocker in a plane parallel to the brush holder's rotation of axis is not transmitted. Besides its articulation about the articulated axis, the articulated connection between the bristle holder and the transmission member may have a further degree of freedom that allows corresponding free movement of the transmission member relative to the bristle holder. More particularly, a translatory motion may occur between the drive rocker and bristle holder along the articulated axis. To this end, the end of the drive rocker facing the brush head may be coupled with the brush head by a groove-shaped recess that cancels out the longitudinal motion of the driver rocker's free end along the groove. As a result only movement that is essentially perpendicular to this groove is transferred to the brush head by the drive rocker.

In an alternative embodiment, the bristle holder may be disposed on the handpiece so as to be displaceable along the bristle holder's axis of rotation. This allows for a second drive motion of the bristle holder, particularly a reciprocating motion parallel to the main axis of the bristles. To this end, the circular movement of the end of the drive rocker facing the bristle holder is transmitted to the bristle holder in two axes. Besides being converted into rotary movement of the bristle holder about its axis of rotation, the motion of the end of the drive rocker closest to the bristle holder is also transferred to the bristle holder in the direction of the axis of rotation, so that the bristle holder executes a translatory back and forth motion along its axis of rotation. For this purpose, the articulated connection between the bristle holder and the drive rocker is equipped with effective transmission means along the articulated axis, which transfer at least some of the corresponding movements of the drive rocker along the articulated axis to the bristle holder. The drive rocker may preferably fit into a recess in the bristle holder, whose lengthwise extension along the articulated axis is smaller than the amplitude of motion in the same direction of the end of the drive rocker that faces the bristle holder.

The motion of the bristle holder may thus be controlled by widening and extending the recess in the bristle holder in which the end of the drive rocker facing the bristle holder is seated. If the end of the drive rocker facing the bristle holder is seated in a recess that extends in the manner of a slot parallel to the bristle holder's axis of rotation, the motion of the driver rocker, or the component of the motion that is parallel to the bristle holder's axis of rotation, is transferred only partially to the bristle holder, or not at all depending on the length of the slot. In contrast, the component of the drive rocker's motion that is perpendicular to the bristle holder's axis of rotation is converted entirely to a rotating oscillating motion of the bristle holder.

On the other hand, if the end of the drive rocker facing the bristle holder is seated in a slot-type recess that extends perpendicularly to the bristle holder's axis of rotation, the drive motion of the driver rocker, or that component of the motion that is perpendicular to the bristle holder's axis of rotation, is converted only partially or not at all into a rotary motion of the bristle holder about its axis of rotation depending on the length of the slot. Meanwhile, the cleaning motion parallel to the bristle holder's axis of rotation is transferred entirely. The respective elements of the motion components that are transferred may be varied correspondingly with elliptical configurations of the recess in the bristle holder in which that end of the drive rocker is seated.

In another embodiment, the bristle holder's axis of rotation extends essentially centrally through the bristle holder and at the same time essentially parallel to the main axis defined by its bristles. This enables the bristle holder to be turned in on itself. If the bristle holder is also displaceable along the axis of rotation, a reciprocating motion may also be effected. If the double conical drive motion of the transmission member is to be used to full advantage, the bristle holder may be secured to the transmission rocker essentially without any play in the direction of the articulated axis, whereas the connection between drive rocker and bristle holder is conformed in articulated manner, preferably in the form of a socket joint, in a direction parallel to the bristle holder's axis of rotation. This enables the angular offset caused by the circulating path of the transmission rocker. This results in an oscillating rotary motion of the bristle holder about its fixed axis of rotation on the toothbrush housing. A reciprocating motion along the axis of rotation is also generated. The double conical movement of the transmission member is converted to motion of the bristle holder in two axes.

The transmission rocker itself advantageously neither rotates about the longitudinal axis nor is translated along the longitudinal axis. This allows for provision of a simple bearing means and simple coupling of the transmission member to the motor, which in turn allows the drive mechanism to be produced considerably more simply and inexpensively. In addition, a simple seal may be provided for the drive mechanism. In particular, a seal for insulating the drive rocker from the toothbrush housing may be formed by the drive rocker bearing. This may be conformed as a bearing ring or sleeve, which is arranged to form an insulating layer between the transmission rocker and the housing. An insulation of this kind in the area of the bearing prevents moisture and dirt or toothpaste from infiltrating the handpiece section of the toothbrush from the brush head section. The insulation is designed as simply and permanently as possible such that relative movement between the drive rocker and the bearing or the insulation is practically eliminated. In particular, translatory or rotary movement of the drive rocker relative to the bearing or the insulation does not occur. The only movement the drive rocker effects consists in traversing a double cone, the vertices of which are located or converge in the area of the bearing or insulation. Accordingly, it is possible, for example, to create the bearing for the drive rocker by spraying an elastic component onto the toothbrush housing. Moreover, the bearing or insulation for the drive rocker may also be assured using a rubber collar, an O-ring, or the like, which is placed over the driver rocker.

In order to be able to adjust the amplitude of the bristle holder's drive motion, it may be provided that the transmission member's bearing is longitudinally movable between the motor and the bristle holder, so that the levering ratios are correspondingly changed on the transmission rocker. In particular, a slidable bearing ring may be used.

The end of the driver rocker facing the motor is coupled to the motor shaft via a cam mechanism. The drive rocker may preferably be connected by an articulation in the manner of a socket joint to a cam that is disposed non-rotatably on the motor shaft, so that the motor end of the drive rocker is driven along a circular track. A particularly simple configuration is achieved if a recess aligned eccentrically to the motor shaft is provided in the cam element on the motor shaft, and in which the transmission member is seated. For practical purposes, the recess is conical in shape or otherwise flared in the direction of the driver rocker to allow for the conical motion.

Advantageously, the one end of the driver rocker is connected directly to the cam on the motor shaft, and the other is connected directly to the bristle holder. The number of components constituting the drive mechanism is thus kept to a minimum.

Of course, the drive rocker may be constructed essentially rigidly, so that the motion generated by the motor at one end of the drive rocker is transferred thereby at its other end to the bristle holder in accordance with the levering ratio. However, the drive rocker may also be made from spring steel wire or some other material with springy properties, such as a plastic rod or similar. This may be used to safeguard against overloading which might otherwise damage the drive mechanism due to excessive driving pressure if, for example, the bristle holder is blocked while the toothbrush in use for cleaning teeth. The drive rocker is preferably constructed as a straight rod, having no protrusions, angles or similar.

For practical purposes, the motor with its drive shaft is aligned longitudinally with the toothbrush and is disposed inside the handpiece. This enables a compact construction of minimal size.

In this respect, a further disadvantage of the hand-held toothbrushes known previously is that attachment and bearing arrangements for the drive motor have proven unsatisfactory. Some expensive and complicated solutions have been suggested, which do not lent themselves to use in the less expensive electric toothbrushes. The rest of the known devices are often to large.

In order to provide a simple method of installing the motor, and a means for securing it that requires minimal space, a chassis for supporting the motor is mounted and may be attached to the inside of a toothbrush housing section. When the motor is secured to the chassis it may be inserted lengthwise with respect to the toothbrush through a frontal opening in the corresponding toothbrush housing section and into the toothbrush housing section, where it is locked securely in place. This allows installation to be considerably simplified. The mechanism is virtually a pre-mounted drive cartridge, which may easily be inserted inside the toothbrush housing and may be locked into place there. The chassis advantageously may be affixed to the toothbrush housing without the use of additional components. Installation is linear, requires no screwing or twisting motion, and may be performed particularly easily and quickly. A twisting motion, such as is required to engage bayonet catches, for instance, is not required. Of course, the special bearing and mounting arrangement for the motor has advantages unrelated to the double conical drive motion of the transmission member described above.

In particular, the chassis supports not only the motor, but also a switching unit with electrical contacts, and is furnished with a battery compartment, into which a battery or rechargeable battery or similar may be inserted. The entire pre-mounted unit, including motor, battery, and switching unit may be pushed like a cartridge into the toothbrush housing in a straight movement without twisting. The locking mechanism that such a movement triggers automatically locks the entire drive unit in place.

In one embodiment, at least one spring-loaded latch hook is provided on the chassis and the toothbrush housing section. The latch hook engages a cooperating latching notch when the chassis is inserted axially. The latch hooks and their counterparts are preferably conformed integrally with the chassis and the toothbrush housing. Separate fixing means do not need to be supplied and considered when mounting.

The latch hooks may be provided on the toothbrush housing, and engage a notch in the chassis. In another embodiment, however, the hooks are provided on the chassis, so that when the chassis is inserted they first spring inwards and slide over and under the housing until they reach the latching notches in the toothbrush housing where they can spring back to their original position. This simple arrangement may serve to ensure that the engagement may be released by pressing the latching tongues inwardly, so that the chassis may be withdrawn and the unit may be disassembled. The latching notches into which the latch hooks spring may be configured as perforations in the toothbrush housing.

To assure that the chassis with the attached motor is positioned precisely and without play relative to the housing, a spring element may be disposed between the chassis and the toothbrush housing, so that it is elastically deformed when the chassis is inserted axially and creates an axial pretension between the chassis and the toothbrush housing. The latching point is thus fixed in a defined position under spring tension even if the latching notch is larger than the latch hook. This also allows a compensation for tolerances. The spring tension means that the latching point is always at the undercut surface of the latch hook.

It may equally be possible to introduce a separate spring element between the chassis and the toothbrush housing. In another embodiment, however, the spring element is conformed integrally with the chassis and/or the toothbrush housing. In particular, spring clips may be provided on the chassis, which press against opposing surface in the housing in the manner of leaf springs and are elastically deformed thereby when the chassis is inserted into the toothbrush housing. The spring clips are preferably located at the leasing end of the chassis as it is inserted into the housing.

In order to prevent the chassis from being inserted in a wrong alignment, an engagement code is preferably provided that allows the chassis to be inserted in one alignment only. In particular a rotational engagement code may provided, thus preventing the chassis from being mounted in a wrong direction. This may serve to ensure that the chassis is always inserted into the housing so that the switching unit lines up under a recess or a corresponding soft plastic section provided in the housing for that purpose.

In one embodiment, an insertion guide particularly in the form of a longitudinal ridge is provided on the chassis and/or the toothbrush housing section. The insertion guide ensures that insertion is taking place with the two parts in the correct alignment. However, it also acts as a means of preventing twisting, which absorbs the reactive forces that are generated when the motor is running. Only axial forces operate on the latching point between the chassis and the toothbrush housing.

In order to seal the toothbrush housing containing the drive cartridge, a housing cap may be placed over the opening in the toothbrush housing. The housing cap may be secured by positive locking. The housing cap then preferably covers a battery compartment provided in the chassis, so that the battery in the battery compartment may be replaced when the housing cap has been removed.

The brush head of the toothbrush may be adapted for various cleaning preferences or conditions or movements. According to one embodiment, the brush head may possess just one bristle cluster, movably arranged on the driven bristle holder.

According to an alternative embodiment, the brush head is furnished with at least one stationary bristle cluster, and one movable bristle cluster which is arranged on the bristle holder. Cleaning is done as with a conventional handheld toothbrush with the stationary bristle cluster, while the movable cluster supplies an additional, motorised cleaning effect.

The movable bristle cluster may be approximately circular in shape, and may be driven in a rotary, oscillating motion about the center point of the circle. The disposition of the movable bristle cluster relative to the stationary bristle cluster may vary. For example, the movable bristle cluster may be located between two stationary bristle clusters. According to one embodiment, the rotary drivable, movable bristle cluster is arranged at a frontal extremity of the brush head, while the stationary bristle cluster is adjacent thereto on the side of the movable bristle cluster that is closest to the handpiece.

The details of one or more embodiments are set forth in the accompanying drawings and the description below. Other features, and advantages will be apparent from the description and drawings, and claims.

DESCRIPTION OF DRAWINGS

FIG. 2 is a longitudinal section through the toothbrush of FIG. 1.

FIG. 3 is a longitudinal section through the toothbrush of FIG. 1, which is rotated through 90° and corresponds to the longitudinal plane of symmetry of the toothbrush.

Like reference symbols in the various drawings indicate like elements.

DETAILED DESCRIPTION

Figure 1:
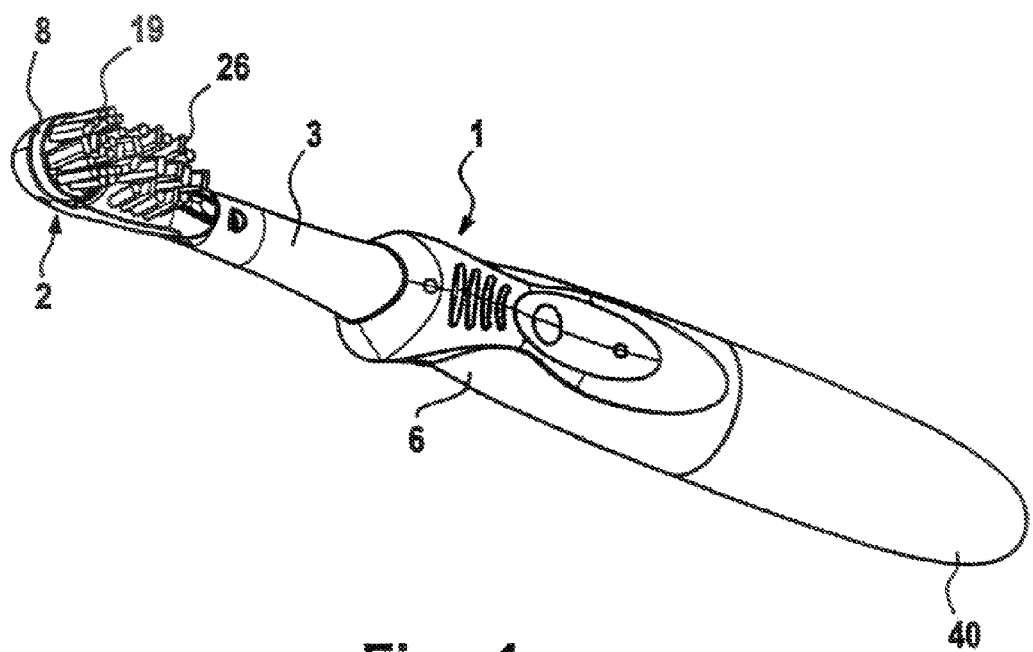
FIG. 1 is a perspective view of an electric toothbrush having one rotatable drivable bristle cluster and one fixed bristle cluster.

Referring to FIG. 1, a toothbrush includes a handpiece 1 and a toothbrush head 2 that is connected to handpiece 1 by a brush tube 3. Arranged one behind the other in handpiece 1 are a battery compartment 5 and an electric motor 4, which is located inside housing 6 and between the battery compartment and brush tube 3. Motor 4 may be switched on and off using a switching element 7 that is disposed on housing 6.

A bristle holder 8 is movably supported and moved on brush head 2, as will be explained in the following. A transmission member 9 that is disposed inside brush tube 3 transfers motive power from motor 4 to bristle holder 8 (see FIGS. 2 and 3).

As shown in FIGS. 2 and 3, motor 4 together with its motor shaft 10 is arranged lengthwise with respect to the toothbrush inside housing 6. A drive rocker 12 is provided as a transmission member, which is configured as a rigid metal rod in the illustrated embodiment. Driver rocker 12 is disposed between motor 4 and bristle cluster 8 so as to be tiltable in multiple axes.

Figure 4:
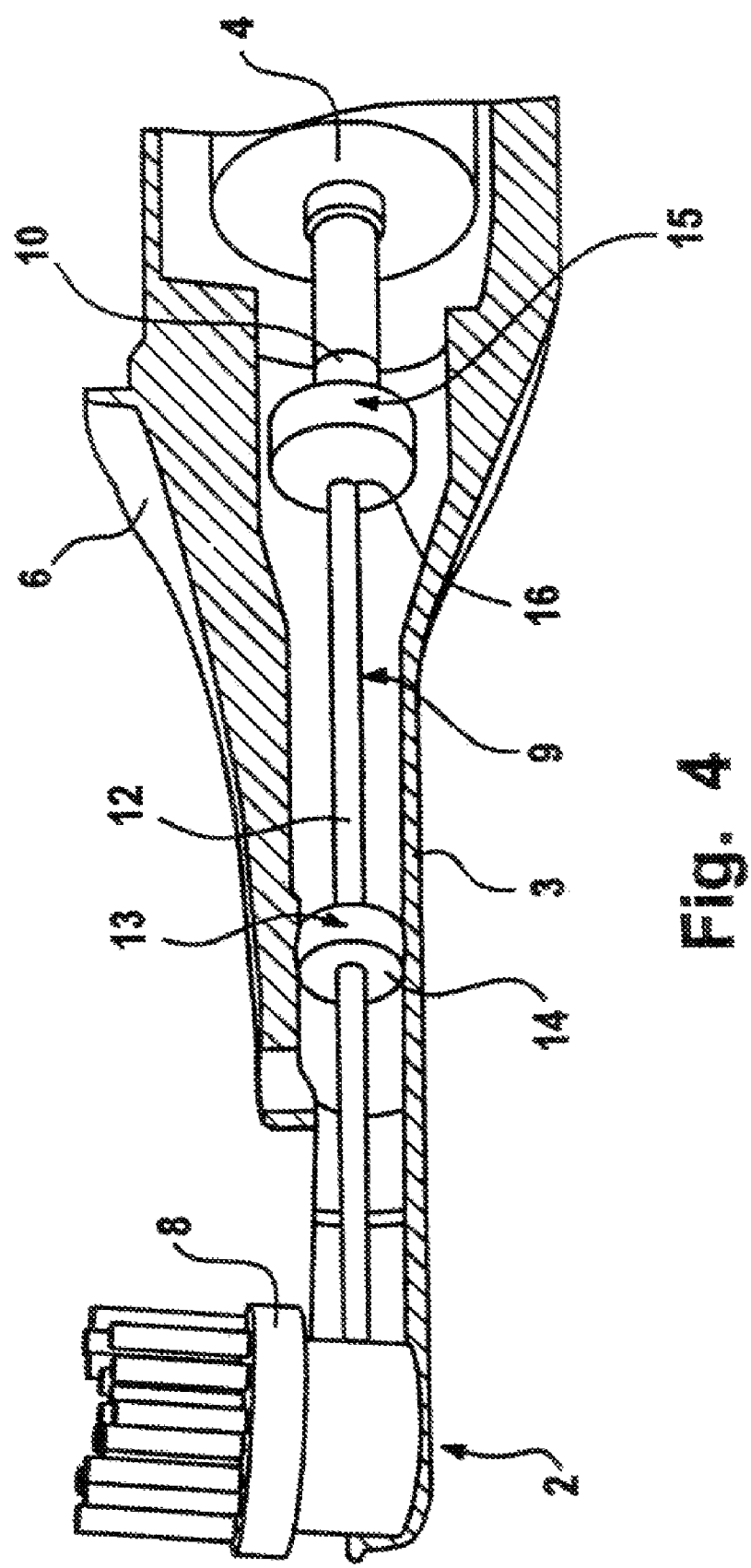
FIG. 4 is a schematic perspective and enlarged representation of the drive for the movable bristle cluster of the toothbrush showing the bearing for a drive rocker between the bristle holder and the motor.

As shown in FIG. 4, a sleeve or ring-shaped bearing member 13 is provided and surrounds drive rocker 12. The ring-shaped securing element permits the drive rocker to move in multiple axes, about swivelling axes that are in a plane perpendicular to the lengthwise direction of the toothbrush.

In order to be able to adjust the levering ratios of the drive rocker, bearing element 13 may be arranged so that it may be moved, particularly slid, in lengthwise direction 11 (shown in FIGS. 2 and 3). On the other hand, FIGS. 2 and 3 show an embodiment in which bearing element 13 is fixed in the brush tube in the manner of a plug. In order to allow the element to be moved, an extension of element 13 might protrude through an aperture (not shown) in the brush tube to serve as an operating element that may be used to displace bearing element 13 lengthwise in the tube. Bearing element 13 includes a ring made from elastic material that surrounds and sealingly encloses drive rocker 12. Facing the outside, the ring or bearing element 13 also extends or is located in the manner of a seal 14 along housing 6, so that the interior of housing 6, in which motor 4 is located, is insulated from brush head 2. Motor 4 is thus insulated from water that may penetrate the housing.

Referring to FIG. 4, drive rocker 12 is coupled to motor 4 via a cam 15. Cam 15 is conformed as a bushing and is disposed in a fixed manner on motor shaft 10. A recess 16 provided in cam 15 is eccentric to motor shaft 10, and receives the motor end of drive rocker 12. Recess 16 is conformed in such a manner that drive rocker 12 is able to execute tilting movements relative to cam 15.

As shown in FIGS. 2 and 3, recess 16 is shaped like a funnel, the mouth of which faces towards drive rocker 12 to allow angular displacement to occur as the rocker is driven. In particular, the motor cam may be furnished with a hole having a correspondingly significant phase or sufficient radius eccentric to motor axle 10. Drive rocker 12 is thus connected to cam 15 by an articulated joint.

Figure 5:
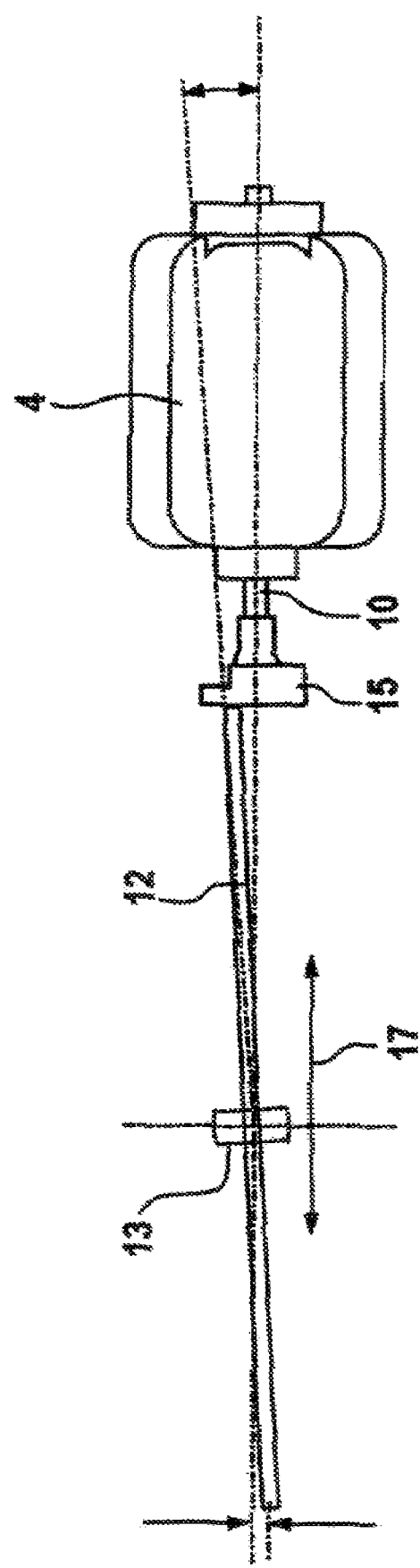
FIG. 5 is a schematic representation of the geometric and kinematic relationships in the drive train, illustrating the double conical drive motion of the transmission member between the motor and the bristle holder.

The driving motion that is engendered in drive rocker 12 by the articulated joint with cam 15 is illustrated in FIG. 5. The end of drive rocker 12 at the motor end moves in a circular path about the motor axle in accordance with the motion of recess 16 in cam 15. The bearing of drive rocker 12 between the motor and the bristle holder, in the form of bearing member 13, fixes driver rocker 12 at a single point, so that the drive motion of driver rocker 12 describes a double conical path. The vertices of both converging cones are in the area of bearing member 13. The levering ratios may be altered by moving bearing member 13 longitudinally towards the motor axle as indicated by arrow 17 in FIG. 5. Depending on the position of bearing member 13, the end of drive rocker 12 that connects with the bristle holder may be induced to describe a circle whose diameter is smaller, larger, or the same size as the circle that is described by the end of drive rocker 12 that is closest to the motor.

Referring again to FIG. 3, bristle holder 8 is supported on the brush head portion of the housing, and is not attached to driver rocker 12. Bristle holder 8 is disposed so that it may rotate about an axis of rotation 18 of the bristle holder, which has the form, as shown in FIG. 3, of a pivot pin that is anchored in the brush head on which the bristle holder is disposed. The bristle holder's axis of rotation 18 may be set at any angle. It preferably extends perpendicularly to longitudinal axis 11 of the toothbrush. In the embodiment shown, it is at right angles to longitudinal axis 11 of the toothbrush and passes through the center of the bristle holder, thereby approximately forming the axis of symmetry of circular bristle cluster 19.

Figure 6:
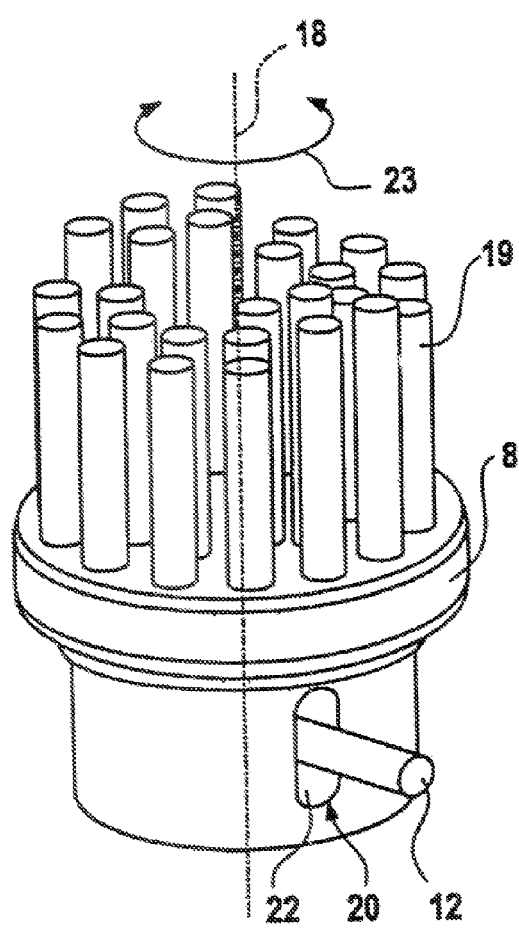
FIG. 6 is a sectional and enlarged view of the bristle holder, showing the connection between the bristle holder and the transmission member according to one embodiment.

In order to convert the drive motion of drive rocker 12 into the desired drive motion for bristle holder 8, an articulated connection, e.g., provided by a hole 20 (shown in FIGS. 6 and 7) is provided between bristle holder 8 and driver rocker 12. Hole 20 is the key to a number of freedoms. On the one hand, it permits a tilting motion between bristle holder 8 and the drive rocker 12 about an articulated axis 21 (shown in FIG. 3) parallel to the bristle holder's axis of rotation 18. It also permits translatory movements between bristle holder 8 and the end of drive rocker 12 along articulated axis 21 (shown in FIG. 3). In addition, the hole 20 permits compensating movements between bristle holder 8 and drive rocker 12, in the longitudinal direction of drive rocker 12, i.e. drive rocker 12 may be withdrawn from bristle holder 8 longitudinally.

As is shown in FIGS. 2 and 3, the bristle holder end of drive rocker 12 is shaped or conformed as a hemispherical shell. A receiving slot 22 that is conformed in the lateral surface of bristle holder 8 and extends parallel to the bristle holder's axis of rotation 18 is provided in bristle holder 8 to accommodate drive rocker 12. As is shown in FIG. 2, receiving slot 22 is furnished with insertion bevels to the right and left, to facilitate insertion of the end of drive rocker 12. On the other hand, together with the hemispherical shell end of drive rocker 12, the shape of the slot, which flares in the direction of drive rocker 12, also permits articulated movement between these two components about articulated axis 21 (see FIG. 3). Because drive rocker 12 is able to slip backwards and forwards in notch 22 in bristle holder 8, only that component of the conical movement which is perpendicular to the bristle holder's axis of rotation 8 is transmitted. The component of the conical movement that is shown as vertical in FIG. 3 is absorbed by the slot or notch-shaped absorbing mechanism 22. The driver rocker's motion parallel to the bristle holder's axis of rotation has no effect. This is shown particularly in FIG. 6.

Figure 7:
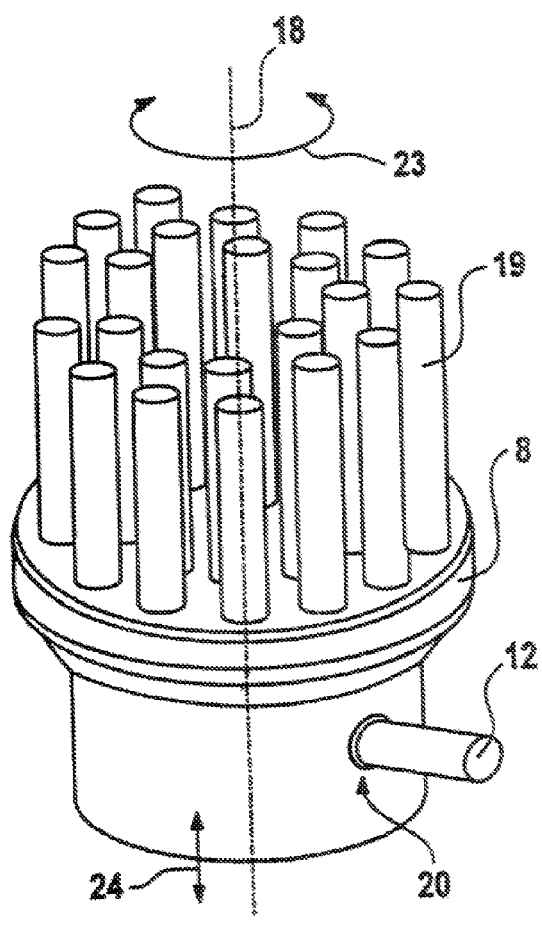
FIG. 7 is an enlarged section representation of the bristle holder, showing the connection between the bristle holder and the transmission member according to an alternative embodiment.

FIG. 7 shows an alternative connection between the bristle holder and drive rocker 12. Here, a socket-type connection is provided which transfers the drive motion of the drive rocker both perpendicular and parallel to the bristle holder's axis of rotation 18. As is shown in FIG. 7, the bristle holder end of drive rocker 12 is seated in a hole 20 in bristle holder 8 which is flared in a funnel shape or is chamfered or rounded towards driver rocker 12 to permit the corresponding angular offset between bristle holder 8 and the drive rocker. The end of drive rocker 12 is preferably also conformed as a hemispherical shell, as in the embodiment described above.

Unlike the embodiment described above, bristle holder 8 is mounted not only so that it may rotate about axis of rotation 18, but also so that it may move along axis of rotation 18. As a result, bristle holder 8 and the bristle cluster located thereon may execute not only oscillating rotary movements about axis of rotation 8, but also reciprocating movements, as indicated by arrows 23 and 24 in FIG. 7. In all other respects, the mounting of bristle holder 8 is the same as was described previously.

If the receiving hole 20 is slightly ovally elongated in the vertical direction, that is to say along the bristle holder's axis of rotation 18, in full oscillation only a corresponding proportion of the travel is transferred. If so desired, the rotary oscillating motion may also be restricted. For this, a hole that is slightly ovally elongated in the horizontal direction would be required. The alignment and shape of the recess in the bristle holder in which the drive rocker is seated may be used to control the motion or the transmission of the drive movement.

Considerable advantages may be derived from the double conical drive motion described in the aforegoing. A simple motor cam without any additional steel pin or similar may be used. The transmission member is seated in a simple recess on the cam. The transmission member may be a simple, straight rod, for example in the form of a wire. Because the transmission member is straight, assembly may be made simple. Length tolerances in the housing are compensated by corresponding geometry in the motor cam and in the connection to the driven member. Tolerances of up to 2.5 mm may be compensated without difficulty. Even though the bearing arrangement for the transmission member is very simple, it is still possible to add a translatory component to the oscillating motion of the bristle holder about is axis of rotation, which has the effect of providing a reciprocating action for cleaning teeth. The angle of oscillation may also be adjusted by changing the drive rocker's bearing point.

As is shown in FIG. 3, bristle holder 8 is preferably circular in shape for rotary drive. The bristle tufts arranged on the bristle holder may be disposed at varying inclinations. According to FIG. 3, the tufts that are located on the periphery are set at a slight angle extending conically outwards, whereas the tufts towards the center are disposed approximately parallel to the bristle holder's axis of rotation.

As shown in FIG. 7, movable bristle cluster 19 is located on the front extremity of the toothbrush. Stationary bristle cluster 26 (shown in FIG. 1), whose tufts are rigidly attached to brush head 2, is arranged adjacently on the brush tube 3 side. The bristle tufts may be deployed in various arrangements. Accordingly to FIG. 3, they are inclined in opposing directions along the lengthwise axis of the toothbrush. Preferably, the distal ends of the bristle tufts may also define varying heights, and such may equally apply to the movable bristle cluster.

Figure 8:
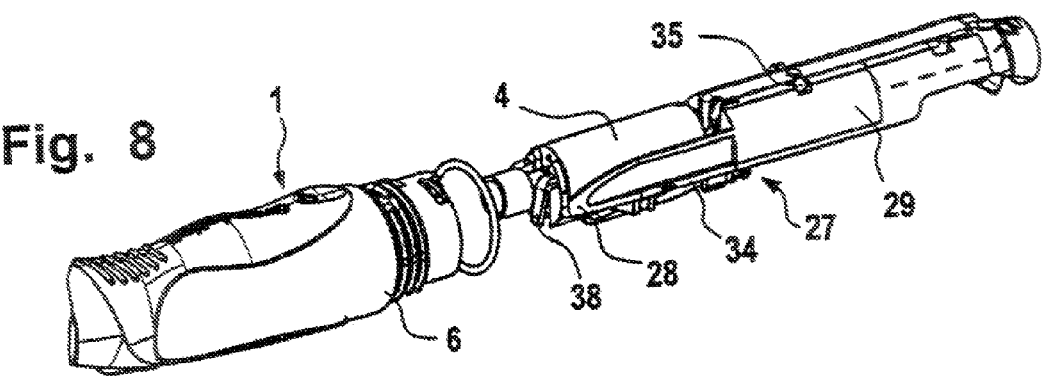
FIG. 8 is a partially exploded view of the toothbrush of FIG. 1, showing a chassis that may be inserted into the toothbrush housing, with the motor secured thereto, a switching unit, and a battery compartment prior to mounting.

Referring to FIG. 8, a chassis 27 is provided to support electric motor 4 inside toothbrush housing 6. Chassis 27 serves as a base for electric motor 4 and is secured to toothbrush housing 6. Both toothbrush housing 6 and chassis 27 are made from injection molded plastic parts and both have an elongated shape with a more or less circular profile. As is shown in FIG. 8, chassis 27 includes a section 28 for securing the motor. Section 28 is configured as a compartment in which the roughly cylindrical electric motor fits snugly. Axially behind motor securing section 28, chassis 27 is conformed as a battery compartment 29, in which a battery or similar device may be inserted, so that the frontal surface thereof abuts with the rear of motor 4. Spring-loaded electrical contacts 30 (shown in FIG. 10) are provided on chassis 27 at the axial ends of battery compartment 29.

Figure 9:
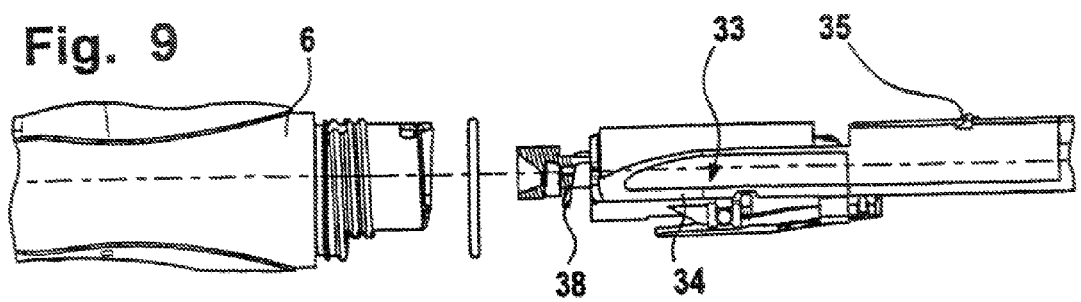
FIG. 9 is an exploded view of the toothbrush of FIG. 1, showing the housing and the chassis in a side view.
Figure 10:
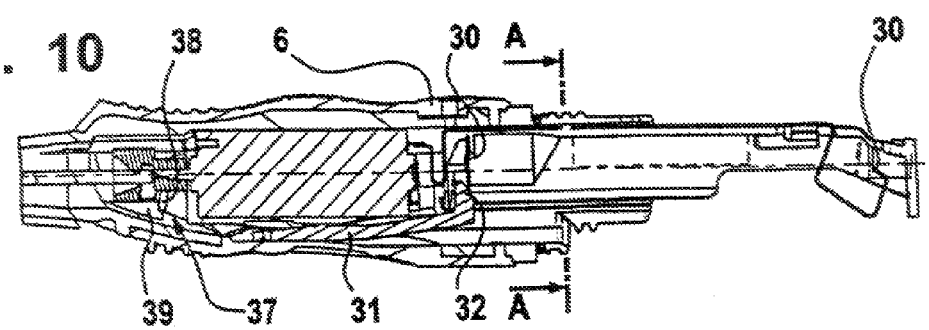
FIG. 10 is a longitudinal view of a section of the toothbrush showing the arrangement of the chassis supporting the motor inside the toothbrush housing after assembly.
Figure 12:
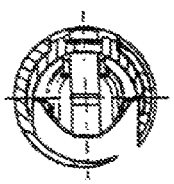
FIG. 12 is a cross-section along line A-A in FIG. 10.

As shown in FIG. 10, in order to be able to switch electric motor 4 on and off, a contact breaker 31 is provided. Contact breaker 31 is attached to chassis 27. As is shown in FIGS. 9 and 10, contact breaker 31 is conformed as a rocker switch that has a hook-shaped overhand 32 for breaking contact. When it is operated in the corresponding manner, contact breaker 31 breaks the contact between a battery in battery compartment 21 and one of electrical contacts 30. In the embodiment shown, operation of contact breaker 31 causes the battery to be moved towards the rear, that is to the right in FIG. 10, so that it is removed from the electrical contact forward thereof. The length of battery compartment 29 is designed to allow the battery to be moved away from the electrical contact. Contract breaker 31 extends axially and is arranged so that is lies directly below an operation recess in the toothbrush housing. The operation recess is covered by a soft plastic membrane which seals the operation aperture in the housing and permits contact breaker 31 to function by elastic deformation (see FIG. 10). The contact breaker rocker returns under its own tension to the position that disconnects the battery from its corresponding contact. The device is arranged so that pressure may be applied through the operating recess in the contact housing either in front of or behind the location of breaker rocker, to allow operation in either direction with a simple press of the thumb.

Chassis 27, which together with the attached electric motor 4, the battery inserted in battery compartment 29, the electrical contacts and the switching unit in the form of contact breaker 31, constitutes a pre-assembled drive unit in the form of a drive cartridge. Chassis 27 may be inserted particularly easily from the rear into toothbrush housing 6 in a straight motion. Toothbrush housing 6 has a frontal or end opening through which the pre-assembled drive cartridge may be inserted, from the back.

In order to assure correct insertion in the desired alignment, an insertion guide 33 is provided between housing 6 and chassis 27. As is shown in FIG. 9, guide ribs 34 are provided approximately in diametric opposition on a lateral surface of chassis 27, and project radially from chassis 27. Insertion grooves or ridges are provided on the internal wall of housing 6 that correspond with these ribs, and into or between which the guide ribs 34 on the chassis are inserted. If guide ribs 34 are not inserted between the mating grooves or ridges in housing 6, they render insertion impossible. They thus constitute a code ensuring that chassis 27 may only be inserted if it is in the correct alignment. At the same time, they prevent the chassis and the motor attached thereto and the switching unit from becoming twisted in the housing.

Figure 11:
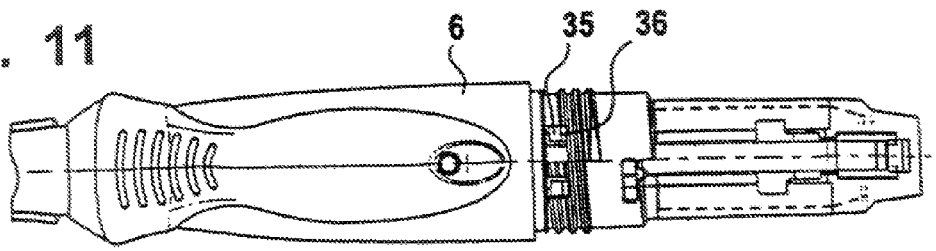
FIG. 11 is a side view of a section of the toothbrush with the battery compartment covering unscrewed, showing the locking arrangement in the form of latch hooks between the chassis supporting the motor and the toothbrush housing.

Chassis 27 with the attached drive elements is secured in housing 6 by positive locking without separate securing means. An engagement point is provided between housing 6 and chassis 27. As is shown in FIGS. 8 and 9, latch hooks 35 that flex radially outwards are provided on a lateral surface of chassis 27 and press against a housing wall as chassis 27 is inserted. If chassis 27 is inserted too far, latch hooks 35 flex radially inwards or the corresponding housing wall of housing 6 flexes radially outwards. When chassis 27 is in the correct position, latch hooks 35 engage with matching notches or latching recesses 36 in the housing wall. As is shown in FIG. 11, two perforations are provided in the housing wall to form latching recesses 36. For an easy snap-on engagement, latching recesses are conformed slightly larger than latch hooks 35, so that the hooks snap easily into place. In order to ensure exact seating, and also to provide compensation for tolerances, chassis 27 is pretensioned in its correct position. Chassis 27 is pressed to the rear, i.e. out of the housing by a spring arrangement 37. Of course, chassis 27 is not actually forced out of the housing, but is pressed with latch hooks 36 against the corresponding counter surfaces on latching recesses 36 so that chassis 27 is always in its correct position. The correct position is defined by the locking flanks of latch hooks 35. In the illustrated embodiment, spring arrangement 37 is integrally moulded on chassis 27. Two spring-loaded clip catches 38 (see FIGS. 8 and 9) are disposed on the frontal face of the chassis, and are designed to deform elastically in axial direction. Stops 39 are provided inside housing 39, against which clip catches 38 are pressed when chassis 27 has been fully inserted into housing 6. This causes clip catches to deform elastically and exercise the desired pretension on chassis 27 in it correct position.

As chassis 27 is being inserted, or immediately thereafter, transmission rod 9 is coupled with cam 15 which is located on motor shaft 10. At this point it is helpful that recess 16, in which transmission rod 9 is seated, flares in a funnel shape in the direction of transmission rod 9 (see FIG. 10). This makes it easier for transmission rod 9 to pass through recess 16.

As is shown in FIG. 11, when assembled, chassis 27 with battery compartment 29 protrudes from the rear of the front housing part. The handpiece consists of two housing parts. The housing section into which the chassis is inserted and to which it is secured is closed with a housing cap 40, which slides over the protruding portion of chassis 27 and is screwed onto the front housing part (see FIG. 1).

What is claimed is:

1. An electric toothbrush comprising
a graspable housing comprising a head portion;
a bristle holder arranged on the head portion of the housing and rotatable about an axis of rotation of the bristle holder, the bristle holder carrying a cluster of bristles; and
a drive mechanism for the bristle holder, including
a motor arranged within the housing, and
a transmission member configured to transfer a driving motion from the motor to the bristle holder, the transmission member including a drive rocker arranged to rock in multiple axes and arranged to be driven by the motor to approximately traverse a double conical path, the drive rocker and the bristle holder being connected in a jointed manner about an articulated axis that is parallel to the axis of rotation of the bristle holder,
wherein the bristle holder is arranged in the housing to move along the articulated axis, and wherein a connection between the bristle holder and the drive rocker transfers at least some corresponding movements of the drive rocker along the articulated axis to the bristle holder.

2. The toothbrush of claim 1, wherein the drive rocker is seated in a recess, a lengthwise extension of which along the articulated axis is smaller than an amplitude of motion of the drive rocker along the articulated axis.

3. The toothbrush of claim 2, wherein the recess in which the drive rocker is seated is a flared hole.

4. The toothbrush of claim 1, wherein the bristle holder is seated on the drive rocker without substantial play along the articulated axis.

5. The toothbrush of claim 1, wherein a bearing member displaceable longitudinally relative to the toothbrush is provided for bearing the transmission member between the motor and the bristle holder.

6. The toothbrush of claim 5, wherein the bearing member comprises a slideable bearing ring.

7. The toothbrush of claim 1, wherein the toothbrush comprises a seal that insulates the transmission member from the toothbrush housing.

8. The toothbrush of claim 1, further comprising a cam coupling an end portion of the transmission member to the motor.

9. The toothbrush of claim 8, wherein the motor comprises a drive shaft on which the cam is fixed non-rotatably, such that the end portion of the transmission member is driven in a circular path.

10. The toothbrush of claim 1, wherein the transmission member comprises a unitary rod.

11. The toothbrush of claim 10, wherein the unitary rod is a straight wire.

12. The toothbrush of claim 1, wherein the transmission member comprises steel.

13. The toothbrush of claim 1, wherein the transmission member comprises a polymeric material.

14. The toothbrush of claim 1, wherein a drive shaft supports the motor longitudinally relative to the toothbrush.

15. The toothbrush of claim 1, wherein the bristle holder carries only one movable bristle cluster.

16. The toothbrush of claim 1, wherein the toothbrush comprises at least one stationary bristle cluster and one movable bristle cluster on the bristle holder.

* * * * *

UNITED STATES PATENT AND TRADEMARK OFFICE
CERTIFICATE OF CORRECTION

PATENT NO. : 7,377,000 B2 Page 1 of 1
APPLICATION NO. : 11/613640
DATED : May 27, 2008
INVENTOR(S) : Michael Drössler et al.

It is certified that error appears in the above-identified patent and that said Letters Patent is hereby corrected as shown below:

On the title page item (57), Line 9 of Abstract;

Delete [is] and Insert --it--

Signed and Sealed this

Fifth Day of August, 2008

JON W. DUDAS
*Director of the United States Patent and Trademark Office*